United States Patent
Rodefeld et al.

(10) Patent No.: US 7,642,371 B2
(45) Date of Patent: Jan. 5, 2010

(54) PROCESS FOR PREPARING DIALKYL THIODIGLYCOLATES

(75) Inventors: Lars Rodefeld, Leverkusen (DE); Witold Broda, Neunkirchen-Seelscheid (DE); Joachim Sommer, Wolfersheim (DE); Joachim Westen, Solingen (DE); Hartmut Richter, Langenfeld (DE)

(73) Assignee: SALTIGO GmbH, Langenfeld (DE)

( * ) Notice: Subject to any disclaimer, the term of this patent is extended or adjusted under 35 U.S.C. 154(b) by 0 days.

(21) Appl. No.: 12/336,618

(22) Filed: Dec. 17, 2008

(65) Prior Publication Data

US 2009/0163736 A1    Jun. 25, 2009

(30) Foreign Application Priority Data

Dec. 21, 2007  (DE) .................. 10 2007 062 282

(51) Int. Cl.
 *C07C 323/22* (2006.01)
(52) U.S. Cl. .................................................. 560/154
(58) Field of Classification Search ................ None
See application file for complete search history.

(56) References Cited

U.S. PATENT DOCUMENTS 2,262,686 A * 11/1941 Kyrides et al. .............. 560/154
2,425,225 A    8/1947  Bearse et al. ............... 260/481
5,773,641 A    6/1998  Labat et al. ................. 560/147
6,869,729 B1   3/2005  Pope et al. .................. 429/213

OTHER PUBLICATIONS

Schulze, Zeilschrift fur Chemie, 1865, p. 78.
Seka, Berichte, 58, 1925, p. 1786.
Database WPI Week 199105; Thomson Scientific, London, GB; AN 1991-033737; XP002522073 & JP02304061 A (Barait Kogyo KK) Dec. 17, 1990.

* cited by examiner

*Primary Examiner*—Paul A Zucker
(74) *Attorney, Agent, or Firm*—Michael A. Miller

(57) ABSTRACT

A process is described for preparing alkyl thiodiglycolates of the general formula (I)

$$R\text{—OOC—CH2-S—CH2-COO—}R \qquad (I)$$

where R is a radical of branched or unbranched $C_1$ to $C_{10}$-alkyl,
 characterized in that an alkyl haloacetate of the general formula (II)

$$X\text{—CH2-COO—}R \qquad (II)$$

where X is a chlorine or bromine atom and R is as defined for compounds of the formula (I)
 is reacted with an aqueous solution of alkali metal sulphide or alkali metal hydrogensulphide in the presence of an aqueous pH buffer solution in the pH range between 5 and 8, optionally in the presence of a phase transfer catalyst.

10 Claims, No Drawings

PROCESS FOR PREPARING DIALKYL THIODIGLYCOLATES

The invention relates to a novel process for preparing dialkyl $C_1$-$C_{10}$-thiodiglycolates.

Dialkyl thiodiglycolates are important precursors for the preparation of specialty chemicals, for example for use in electronically conductive polymers.

The synthesis of dialkyl thiodiglycolates has already been known in principle for some time.

There are essentially two ways of synthesizing dialkyl thiodiglycolates:

a) esterification of thiodiglycolic acid with alcohols under acidic catalysis.

b) reaction of chloroacetic esters with sodium sulphide.

A significant disadvantage of variant a) is that, for the esterification of thiodiglycolic acid with alcohols with the aid of hydrochloric acid (Schulze, Zeitschrift für Chemie 1865, p. 78) or with the aid of sulphuric acid (Seka, Berichte 58, 1925, p. 1786), crystalline thiodiglycolic acid is required. This means that the very water-soluble thiodiglycolic acid has to be separated from the water phase. This always leaves a portion of the thiodiglycolic acid in the mother liquor and, moreover, the isolation as a solid affords the thiodiglycolic acid together with inorganic salts, and so it has to be recrystallized once more. An esterification from the aqueous solution therefore delivers unsatisfactory results (U.S. Pat. No. 2,425,225).

In order to avoid the complicated isolation of the thiodiglycolic acid as a solid, U.S. Pat. No. 2,425,225 describes a process in which the thiodiglycolic acid is extracted directly from the aqueous phase with the alcohol to be esterified. However, this process only works with alcohols having more than three carbon atoms and is therefore unsuitable for the synthesis of methyl, ethyl and propyl thiodiglycolate, since the corresponding alcohols having fewer than four carbon atoms are fully soluble in water and therefore cannot function as extractants.

A particular difficulty in the reaction of chloroacetic esters with sodium sulphide is that sodium sulphide is a very strong base, while chloroacetic esters are very pH-sensitive and hydrolyse readily.

When an aqueous sodium sulphide solution is passed into methyl chloroacetate, owing to the hydrolysis of the reactant and/or of the product, only moderate yields of methyl thiodiglycolate are obtained. In WO 00/45451, a yield of 39% is reported in the reaction of ethyl bromoacetate with sodium sulphide.

One means of avoiding the hydrolysis of the chloroacetic ester is, as described in U.S. Pat. No. 2,262,686, to perform the reaction in an inert solvent such as acetone. In this anhydrous variant for the synthesis of thiodiglycolic esters, anhydrous sodium sulphide is required, which is significantly more expensive than hydrous sodium sulphide, and the reaction time is disproportionately long at 15 to 20 h of boiling under reflux.

It was an object of the present invention to provide a process for preparing a dialkyl thiodiglycolate, which affords the desired product in a simplified manner and with a better yield than according to the prior art to date.

It has been found that, astonishingly, by virtue of the establishment of suitable reaction conditions, the reaction of methyl chloroacetate with alkali metal sulphide or alkali metal hydrogensulphide to give dimethyl thiodiglycolate in aqueous solution does in fact deliver very high yields. What is crucial is that the sulphide compound is depleted quickly, and hence the pH in the solution is kept within the range of 5<pH<8.

The invention therefore provides a process for preparing alkyl thiodiglycolates of the general formula (I)

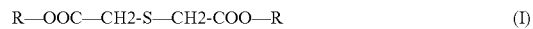

where R is a radical of branched or unbranched $C_1$ to $C_{10}$-alkyl, wherein an alkyl haloacetate of the general formula (II)

where X is a chlorine or bromine atom and R is as defined for compounds of the formula (I)

is reacted with an aqueous solution of alkali metal sulphide or alkali metal hydrogensulphide in the presence of an aqueous pH buffer solution in the pH range between 5 and 8, optionally in the presence of a phase transfer catalyst.

The aqueous buffer solution is preferably a dialkali metal hydrogenphosphate or alkali metal dihydrogenphosphate or ammonium acetate or ammonium chloride buffer solution. Examples of dialkali metal hydrogenphosphate are $K_2HPO_4$ or $Na_2HPO_4$; examples of alkali metal dihydrogenphosphate are $KH_2PO_4$ and $NaH_2PO_4$.

The sulphide sources used may be aqueous solutions either of alkali metal sulphide (sodium or potassium sulphide) or of alkali metal hydrogensulphide (sodium or potassium hydrogensulphide). The concentration of the aqueous alkali metal sulphide solution is between 5 and 20% by weight and that of the alkali metal hydrogensulphide solution is between 5 and 50% by weight.

The reagents can be metered into the aqueous buffer solution with stirring in a manner known per se, for example in a heatable jacketed vessel by means of pumps, through suitable lines or by means of a static mixer.

Typically, the $C_1$-$C_{10}$-alkyl haloacetate is metered in together with the alkali metal sulphide or alkali metal hydrogensulphide in a molar ratio between 1:1 to 3:1. This molar ratio is preferably 2:1. The metered addition can be effected simultaneously or in portions, but preferably simultaneously.

The simultaneous metered addition is effected generally over a period of from 0.5 to 24 hours. The temperature at which the metered addition is effected should be in the range between 10 and 60° C., preferably 20 to 40° C.

Optionally, the reaction can be carried out in the presence of a phase transfer catalyst. Examples of suitable commercially available catalysts are tetrabutylammonium chloride, tributylmethylammonium chloride, methyltrioctylammonium chloride, methyltridecylammonium chloride, polyethylene glycol 400-40 000, crown ethers, tris[2-(2-methoxyethoxy)ethyl]amine or trialkylphosphonium salts. Preference is given to using tetrabutylammonium chloride or polyethylene glycol 400 as the phase transfer catalyst.

It has to be ensured that the pH during the reaction is kept between 5 and 8.

On completion of reaction, the crude product is removed from the aqueous buffer solution. This can be done, for example, by extraction. To this end, the reaction solution is admixed with a water-immiscible solvent and the aqueous phase is removed from the organic phase.

The extractant can then subsequently be removed from the organic phase, for example by distillation. The residue contains the desired product in yields of 88 to 95% of theory.

The extractants used to remove the crude product from the aqueous buffer solution may be branched or unbranched C$_2$-C$_4$-dialkyl ethers, such as diethyl ether (DEE) and methyl tert-butyl ether (MTBE), or branched or unbranched dialkyl ketones, such as methyl isobutyl ketone (MIBK), or branched or unbranched C$_4$-C$_{10}$-hydrocarbons such as pentane, hexane, heptane or cyclohexane, or aromatic compounds such as benzene, toluene, xylene or dichlorobenzene. Preference is given to using toluene as the extractant.

The process according to the invention can be used to prepare dialkyl thiodiglycolates with C$_1$-C$_{10}$-alkyl radicals in the ester moieties through the use of the corresponding C$_1$-C$_{10}$-alkyl haloacetates. Preference is given to preparing the C$_1$-C$_4$-alkyl esters, i.e. dimethyl thiodiglycolate, diethyl thiodiglycolate, dipropyl thiodiglycolate or dibutyl thiodiglycolate. Particular preference is given to dimethyl thiodiglycolate and diethyl thiodiglycolate.

The dialkyl thiodiglycolates obtained by the process described can be processed further directly without distillative purification. Owing to the virtually quantitative and rapid conversion of sodium sulphide, neither the extracted air nor the wastewater contains significant amounts of hydrogen sulphide.

The examples which follow are intended to illustrate the invention further, but without restricting its scope.

EXAMPLE 1

In a 1 ltr. jacketed glass reactor, 17.9 g of sodium dihydrogenphosphate dihydrate were dissolved in 84.2 g of water (pH=3.9) and adjusted to pH=6.0 with 6.7 g of sodium hydroxide solution (32%). The buffer solution was warmed to 33° C. and admixed with 13.0 g of tributylmethylammonium chloride solution (75% in water) and 40.0 g of methyl chloroacetate. Simultaneously, 611.2 g of sodium sulphide solution (16% in water) and 182.1 g of methyl chloroacetate were metered in at 30-35° C. within 2 h. Subsequently, a further 19.3 g of sodium sulphide solution (16% in water) were metered in and the mixture was stirred at 33° C. for a further 1 h. The reaction solution was admixed with 130 ml of toluene, stirred vigorously and then the lower phase was removed. After the toluene had been distilled off at approx. 300 mbar, 226.6 g of a clear liquid comprising 93% dimethyl thiodiglycolate and 6% toluene were obtained. This corresponds to a yield of 93% of theory.

EXAMPLE 2

In a 1 ltr. jacketed glass reactor, 35.8 g of sodium dihydrogenphosphate dihydrate were dissolved in 168.4 g of water (pH=3.9) and adjusted to pH=7.0 with 24.4 g of sodium hydroxide solution (32%). The buffer solution was warmed to 33° C. and admixed with 13.0 g of tributylmethylammonium chloride solution (75% in water) and 40.0 g of methyl chloroacetate. Simultaneously, 269.8 g of sodium hydrogensulphide solution (26% in water) and 182.1 g of methyl chloroacetate were metered in at 30-35° C. within 2 h. Simultaneous addition of sodium hydroxide solution (32% in water) kept the pH at 7. Subsequently, a further 8.5 g of sodium hydrogensulphide solution (26% in water) were metered in and the mixture was stirred at 33° C. for a further 1 h. The reaction solution was admixed with 130 ml of toluene and stirred vigorously. Subsequently, the lower phase was removed. After the toluene had been distilled off at approx. 300 mbar, 236.4 g of a clear liquid comprising 91% dimethyl thiodiglycolate and 6% toluene were obtained. This corresponds to a yield of 95% of theory.

EXAMPLE 3

In a 1 ltr. jacketed glass reactor, 17.9 g of sodium dihydrogenphosphate dihydrate were dissolved in 84.2 g of water (pH=3.9) and adjusted to pH=6.0 with 6.7 g of sodium hydroxide solution (32%). The buffer solution was warmed to 33° C. and admixed with 13.0 g of tributylmethylammonium chloride solution (75% in water) and 40.0 g of methyl chloroacetate. Simultaneously, 611.2 g of sodium sulphide solution (16% in water) and 182.1 g of methyl chloroacetate were metered in at 30-35° C. within 2 h. Subsequently, a further 19.3 g of sodium sulphide solution (16% in water) were metered in and the mixture was stirred at 33° C. for a further 1 h. The reaction solution was admixed with 130 ml of toluene and stirred vigorously. Subsequently, the lower phase was removed. After the toluene had been distilled off at approx. 300 mbar, 226.6 g of a clear liquid comprising 93% dimethyl thiodiglycolate and 6% toluene were obtained. This corresponds to a yield of 93% of theory.

EXAMPLE 4

In a 1 ltr. jacketed glass reactor, 35.8 g of sodium dihydrogenphosphate dihydrate were dissolved in 168.4 g of water (pH=3.9) and adjusted to pH=6.0 with 11.4 g of sodium hydroxide solution (32%). The buffer solution was warmed to 33° C. and admixed with 13.0 g of polyethylene glycol 400 and 40.0 g of methyl chloroacetate. Simultaneously, 611.2 g of sodium sulphide solution (16% in water) and 182.1 g of methyl chloroacetate were metered in at 30-35° C. within 2 h. Subsequently, a further 19.3 g of sodium sulphide solution (16% in water) were metered in and the mixture was stirred at 33° C. for a further 2 h. The reaction solution was admixed with 130 ml of toluene and stirred vigorously. Subsequently, the lower phase was removed. After the toluene had been distilled off at approx. 300 mbar, 227.2 g of a clear liquid comprising 88% dimethyl thiodiglycolate, 1% methyl thioglycolate, 1% ethyl chloroacetate and 6% toluene were obtained. This corresponds to a yield of 90% of theory.

EXAMPLE 5

In a 1 ltr. jacketed glass reactor, 15.8 g of glacial acetic acid were dissolved in 168.4 g of water (pH=2.3) and adjusted to pH=6.0 with 19.0 g of aqueous ammonia solution (26%). The buffer solution was warmed to 33° C. and admixed with 16.0 g of tributylmethylammonium chloride solution (75% in water) and 40.0 g of methyl chloroacetate. Simultaneously, 611.2 g of sodium sulphide solution (16% in water) and 182.1 g of methyl chloroacetate were metered in at 30-35° C. within 2 h. Subsequently, a further 19.3 g of sodium sulphide solution (16% in water) were metered in and the mixture was stirred at 33° C. for a further 1 h. The reaction solution was admixed with 130 ml of toluene and stirred vigorously. Subsequently, the lower phase was removed. After the toluene had been distilled off at approx. 300 mbar, 223.8 g of a clear liquid comprising 92% dimethyl thiodiglycolate and 6% toluene were obtained. This corresponds to a yield of 90% of theory.

EXAMPLE 6

In a 1 ltr. jacketed glass reactor, 35.8 g of sodium dihydrogenphosphate dihydrate were dissolved in 168.4 g of water (pH=3.9) and adjusted to pH=6.0 with 12.2 g of sodium hydroxide solution (32%). The buffer solution was warmed to 33° C. and admixed with 13.0 g of tributylmethylammonium chloride solution (75% in water) and 40.0 g of ethyl chloroacetate. Simultaneously, 611.2 g of sodium sulphide solution (16% in water) and 275.3 g of ethyl chloroacetate were metered in at 30-35° C. within 2 h. Subsequently, a further 19.3 g of sodium sulphide solution (16% in water) were metered in and the mixture was stirred at 33° C. for a further 1 h. Subsequently, a further 19.3 g of sodium sulphide solution (16% in water) were metered in and the mixture was stirred at 33° C. for a further 2 h. The reaction solution was admixed with 130 ml of toluene and stirred vigorously. Subsequently, the lower phase was removed. After the toluene had been distilled off at approx. 300 mbar, 277.2 g of a clear liquid comprising 90% diethyl thiodiglycolate and 9% toluene were obtained. This corresponds to a yield of 95% of theory.

The invention claimed is:

1. Process for preparing alkyl thiodiglycolates of the general formula (I)

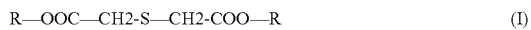
R—OOC—CH2-S—CH2-COO—R          (I)

where R is a radical of branched or unbranched $C_1$ to $C_{10}$-alkyl, wherein an alkyl haloacetate of the general formula (II)

X—CH2-COO—R          (II)

where X is a chlorine or bromine atom and R is as defined for compounds of the formula (I)

is reacted with an aqueous solution of alkali metal sulphide or alkali metal hydrogensulphide in the presence of an aqueous pH buffer solution in the pH range between 5 and 8, optionally in the presence of a phase transfer catalyst.

2. Process according to claim 1, wherein the aqueous buffer solution comprises a dialkali metal hydrogenphosphate buffer, an alkali metal dihydrogenphosphate buffer, a sodium hydrogencarbonate buffer, an ammonium acetate buffer or an ammonium chloride buffer.

3. Process according to claim 1, wherein the pH range is between 6 and 8.

4. Process according to claim 1, wherein the aqueous alkali metal sulphide solution used is an aqueous sodium sulphide solution having a content between 5 and 30% by weight or an aqueous sodium hydrogensulphide solution having a content between 5 and 50% by weight.

5. Process according to claim 1, wherein the alkyl haloacetate of the formula (II) is a methyl, ethyl, propyl, butyl, pentyl, hexyl or cyclohexyl chloroacetate or a methyl, ethyl, propyl, butyl, pentyl, hexyl or cyclohexyl bromoacetate.

6. Process according to claim 1, wherein the alkyl haloacetate of the formula (II) and the alkali metal sulphide or alkali metal hydrogensulphide solution are metered in simultaneously in a molar ratio of 1:1 to 3:1 relative to one another.

7. Process according to claim 1, wherein the temperature of the reaction solution is in the range of 0 to 60° C.

8. Process according to claim 1, wherein the phase transfer catalyst used is tetrabutylammonium chloride, tributylmethylammonium chloride, methyltrioctylammonium chloride, methyltridecylammonium chloride, polyethylene glycol 400-40 000, crown ethers, tris[2-(2-methoxyethoxy)ethyl]amine or a trialkylphosphonium salt.

9. Process according to claim 1, wherein the dialkyl $C_1$-$C_{10}$-thiodiglycolate is removed from the aqueous reaction solution with a water-immiscible organic solvent.

10. Process according to claim 7, wherein the temperature of the reaction solution is in the range of 10 to 40° C.

* * * * *